United States Patent [19]
Bradford

[11] Patent Number: 5,402,672
[45] Date of Patent: Apr. 4, 1995

[54] MICROWAVE OVEN MOISTURE ANALYZER

[75] Inventor: Gary R. Bradford, Wappingers Falls, N.Y.

[73] Assignee: North Atlantic Equipment Sales, Inc., Wappingers Falls, N.Y.

[21] Appl. No.: 111,116

[22] Filed: Aug. 24, 1993

[51] Int. Cl.⁶ .................... G01N 25/26; G01N 5/02
[52] U.S. Cl. ............................ 73/76; 374/14; 177/238; 177/245; 219/708
[58] Field of Search .............. 73/76; 374/14; 177/238, 177/245; 219/708

[56] References Cited

U.S. PATENT DOCUMENTS

| | | | |
|---|---|---|---|
| 3,813,918 | 6/1974 | Moe | 73/76 |
| 3,916,670 | 11/1975 | Davis et al. | 73/76 |
| 4,291,775 | 9/1981 | Collins | 73/76 |
| 4,398,835 | 8/1983 | Athey et al. | 73/76 |
| 4,750,143 | 6/1988 | Heitz et al. | 73/76 |
| 5,085,527 | 2/1992 | Gilbert | 374/14 |

FOREIGN PATENT DOCUMENTS

| | | | |
|---|---|---|---|
| 0725859 | 8/1942 | Germany | 73/76 |
| 3231004 | 2/1984 | Germany | 73/76 |
| 44-23956 | 12/1969 | Japan | 73/76 |
| 0207844 | 12/1982 | Japan | 73/76 |
| 0165038 | 9/1983 | Japan | 73/76 |
| 0604863 | 7/1948 | United Kingdom | 73/76 |

Primary Examiner—Diego F. F. Gutierrez
Attorney, Agent, or Firm—Joseph B. Taphorn

[57] ABSTRACT

A microwave oven moisture analyzer is provided with an analysis chamber using a V-shaped structure wherein the wings extend from a vertical back wall forwardly and outwardly to the side walls of the oven. The upper edges of the wings also rise as the wings extend, to where at their ends they engage the ceiling of the oven. A roof rests on the wings and slopes downwardly rearwardly. The back wall is shorter than the adjacent wing portions and hence an opening exists from the analysis chamber into the rest of the oven. Air flowing down over the roof creates a venturi effect at the opening to remove air from the analysis chamber. A four point arrangement supports a fiber-glass pad bearing a sample in spaced relation to the floor and the sides of the chamber and below the opening so that moisture evaporated does not have a place to condense before it is removed from the chamber. The points are the upper ends of posts integral with a stem extending through the floor of the oven onto the load sensor of a constantly measuring electronic scale connected to a printer and a vacuum flourescent display.

15 Claims, 3 Drawing Sheets

MICROWAVE OVEN MOISTURE ANALYZER

1. Field of the Invention

This invention relates to a microwave oven moisture analyzers, and more particularly, to an improved microwave oven moisture analyzer wherein the moisture evaporated from the sample being analyzed interferes less with the accurate and expeditious conduct of the moisture analysis.

2. Background of the Invention

Moisture analyzers in common use today are microwave ovens modified for laboratory analysis. Such ovens commonly receive air from holes in the ceiling near their front ends and exhaust it through holes in the back wall, for cooling and moisture removal purposes. The modifications include the placement of an electronic analytical balance or scale beneath the floor of the oven. A vertical stem resting on the balancing member or load sensor of the scale projects upwards through the floor of the oven to mount a platform disc or plate upon which a sample to be weighed at the start of the analysis and constantly during desiccation, is placed. The sample normally is placed on the platform via a fiber-glass pad which was previously placed on the platform to zero-in the scale. The electronic scale constantly measures the weight of the sample during the desiccation operation of the microwave oven, and displays the observed weight on a screen; at the end of the drying cycle, it records percent moisture or solids via a printer.

It has been found that moisture evaporated from the sample condenses on the platform and delays processing. The small droplets of the moisture condensation lack the density to turn absorbed energy into enough heat to evaporat effectively, thereby increasing drying time.

It has also been found that condensation and air movement causes erroneous moisture evaporation readings during the process.

3. Prior Art

The prior art includes Pat. No. 3,813,918 issued Jun. 4, 1974 to Moe. Therein the content of the volatized ingredient is determined by measurement of the weight change, while the sample is still in the oven, immediately after application of the microwave energy. Another is Pat. No. Re. 32,861 issued Feb. 7, 1989 to Collins et al. It too shows placing of a sample on a balance, and an electronic readout.

SUMMARY OF THE INVENTION

Accordingly, it is an object of the invention to prevent moisture evaporated from the sample from interfering with the microwave oven moisture analysis of a sample.

A more specific object of the invention is to provide a microwave oven and method for conducting moisture analysis of a sample with reduced interference of the analysis by the moisture evaporated from the sample and by air movement in the oven or cavity.

Another object of the invention is to provide a microwave oven for moisture analysis that is easier to use and processes faster.

Still another object of the invention is provide such a moisture analyzer that is inexpensive and simple of construction, and reliable in operation.

The objects of the invention are accomplished mainly by two improvements in a microwave oven moisture analyzer. It has been discovered that the amount of sample evaporated moisture condensed on a support arrangement can be reduced by eliminating the circular or pan type platform for supporting the sample and substituting a point support arrangement for the fiber-glass pad bearing the sample. The fiber-glass pad has sufficient rigidity and the point support arrangement has an adequate number of points sufficiently closely disposed, to support the pad in a relatively flat way.

An advantage of the invention is that the point support arrangement minimizes contact to facilitate better airflow through the fiber-glass pad and hence abets and speeds the evaporation of the moisture from the sample.

The amount of sample evaporated moisture available to condense on the support arrangement is further reduced by an improved air flow system that also reduces the impact of moving air on the support arrangement. Conventionally, microwave ovens receive fresh air through openings in their ceilings and exhaust heated air and moisture through openings in their back walls.

The second improvement involves muffling the microwave chamber or oven so as not to impede sample heating while facilitating secondary air flow that removes moisture evaporated from the sample before it has a chance to condense on the sample support arrangement. To this end, the scale beneath the floor is located near the front end of the oven and so that the sample support arrangement is near the front of the oven, and a simple, easily inserted and removed structure constructed about the sample support arrangement to reduce the flow of air thereabout while facilitating evaporated moisture removal from about the support arrangement. The structure is formed with an opening above and behind the sample support arrangement, past which the air that the oven receives from the ceiling moves on its way to the exhaust holes in the back wall. In so doing, a venturi effect is created at the support structure hole which gently removes the air containing evaporated moisture from around the sample support arrangement before much of it has a chance to condense on the sample support arrangement.

An advantage of this improvement is that with the sample support arrangement in the front end of the oven, the samples can be easily inserted and removed from the oven.

BRIEF DESCRIPTION OF DRAWINGS OF AN EMBODIMENT

These and other objects, features, advantages of the invention will become apparent from a reading of the following description of a preferred embodiment of the invention, when considered with the attached drawings wherein.

DETAILED DESCRIPTION OF A PREFERRED EMBODIMENT OF THE INVENTION

Figure 1:
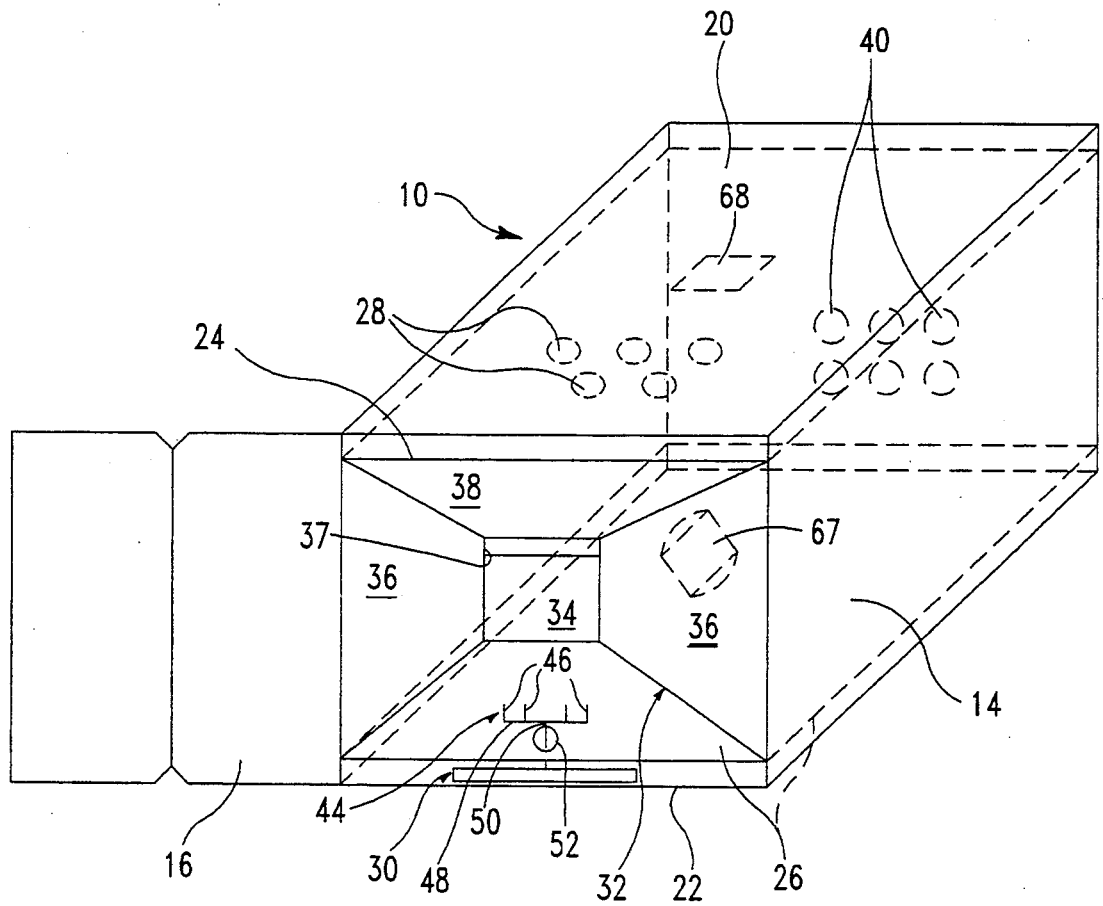
FIG. 1 is diagrammatic isometric view of a microwave oven analyzer improved according to the invention.
Figure 2:
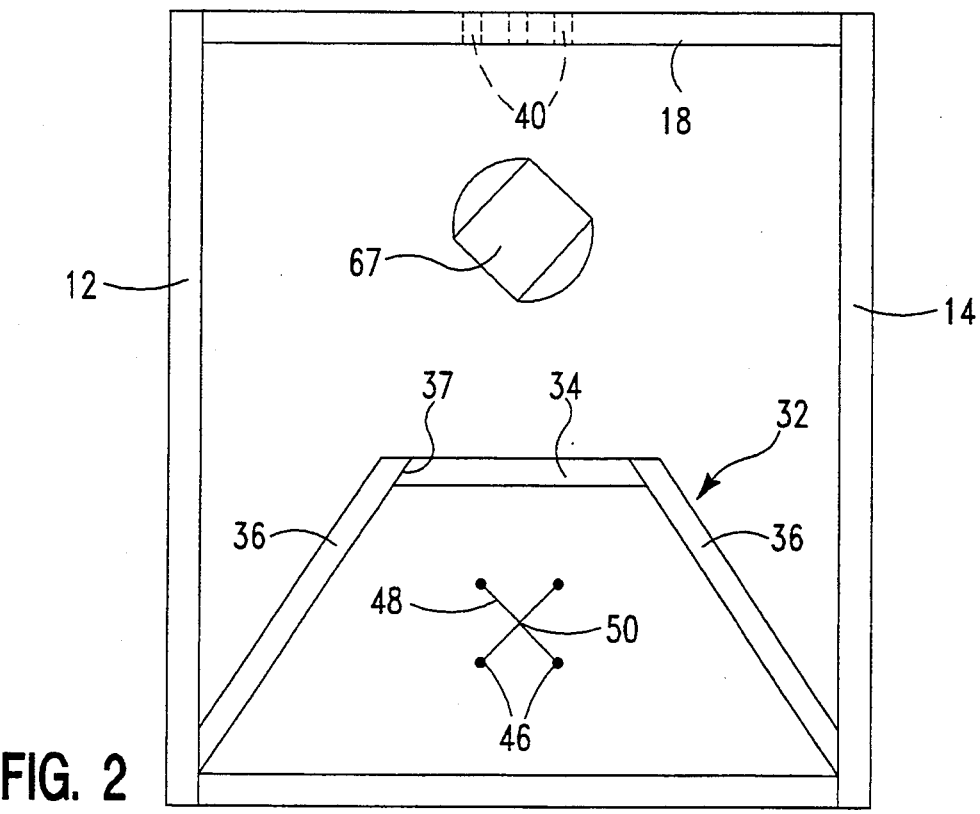
FIG. 2 is a diagrammatic cross-sectional view from above of the oven of FIG. 1.

Referring now more particularly to the drawings, there is diagrammatically shown in FIG. 1 a microwave oven generally indicated by the numeral 10. The oven 10 includes left and right side walls 12 and 14 respectfully, a door 16 and a rear wall 18. A roof 20 and a bottom 22 complete the externals of the oven. The internals include a ceiling 24 spaced from the roof 20, and a floor 26 spaced from the bottom 22. The spacing between the roof 20 and ceiling 24 accommodates among other things the deliverance of air under pressure from a conventional source not shown, to holes 28 formed in the front end of the ceiling 24. The spacing between the floor 26 and bottom 22 accommodates among other things the installation of a commercially available electronic analytical balance or scale, generally indicated by the numeral 30, for taking weight measurements before, periodically during, and after, moisture analysis of a sample in the analysis chamber.

The analysis chamber is formed in the front end of the oven between the ceiling 24 and the floor 26 by a two part muffling structure. The two-part muffling structure includes a generally tapered structure generally indicated by the numeral 32. It consists of a vertical central or back wall portion 34 and vertical, forwardly therefrom diverging side portions or wings 36 having their upper edges uniformly rising towards their free ends. Thus the wings are projecting diagonally forward from the back wall to the side walls of the oven. The upper edges of the side portions 36 begin above the top edge of the central portion 34 to define partially an opening 37 between them.

The other part of the two part muffling structure includes a trapezoidal-shaped, flat structure 38 which rests in slots 39 cut into the side portions 36 to form the analysis chamber ceiling. It extends from the front of the oven to over the vertical central portion 34 where it completes formation of the opening 37.

The two parts of the muffling structure are formed of a microwave transparent material. Suitable materials are high density polyethylene (HDPE) and ultra high molecular weight polyethylene (UHMW).

Figure 3:
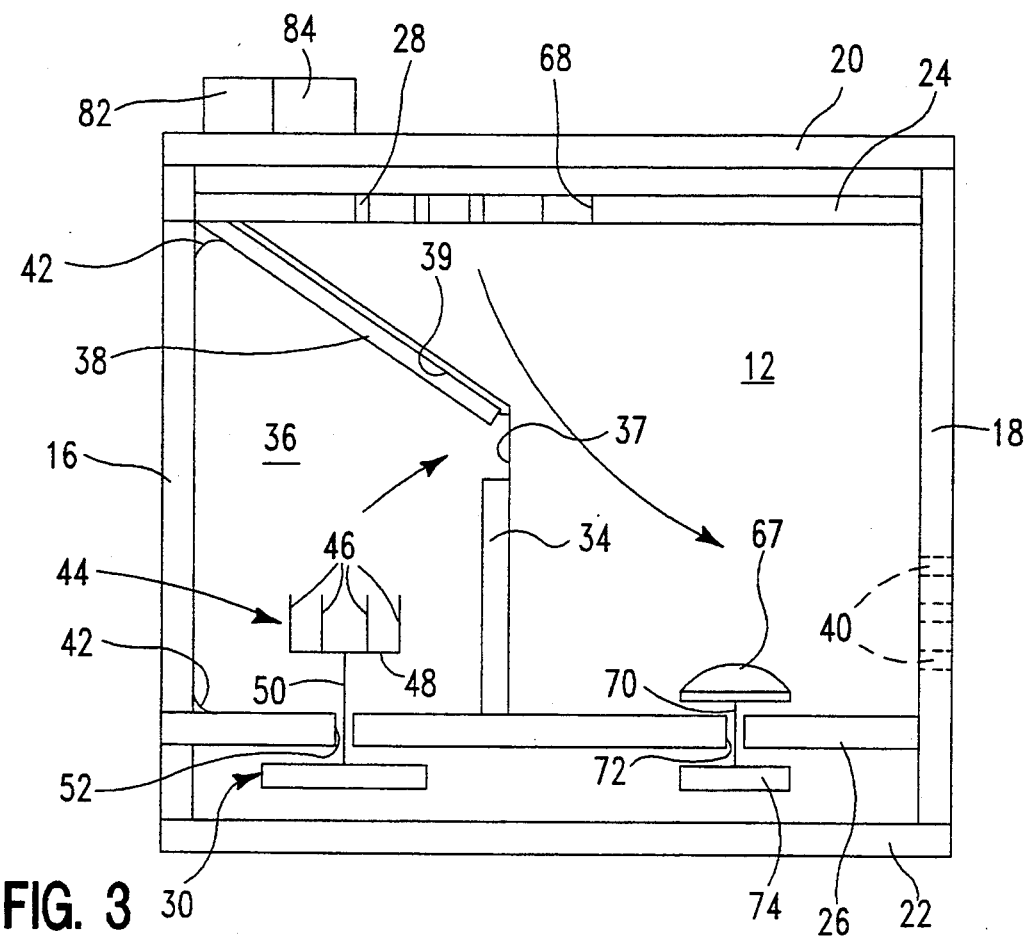
FIG. 3 is a diagrammatic cross-sectional view from the right side of the oven of FIG. 1.
Figure 4:
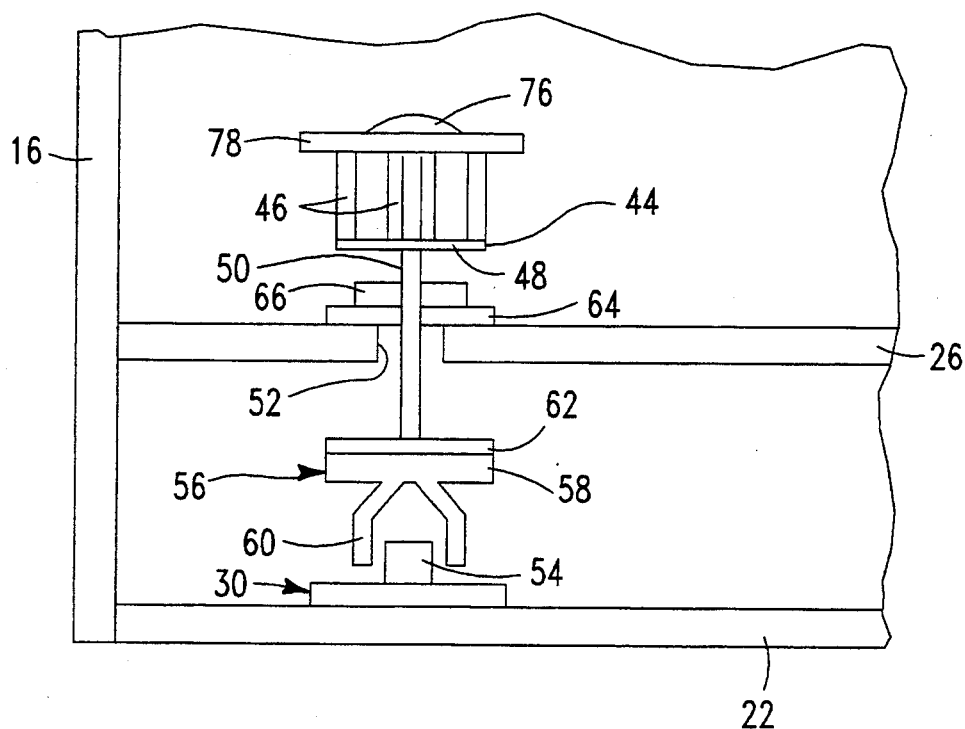
FIG. 4 is an enlarged diagrammatic cross-sectional view from the right side and showing the sample support arrangement in greater detail.
Figure 5:
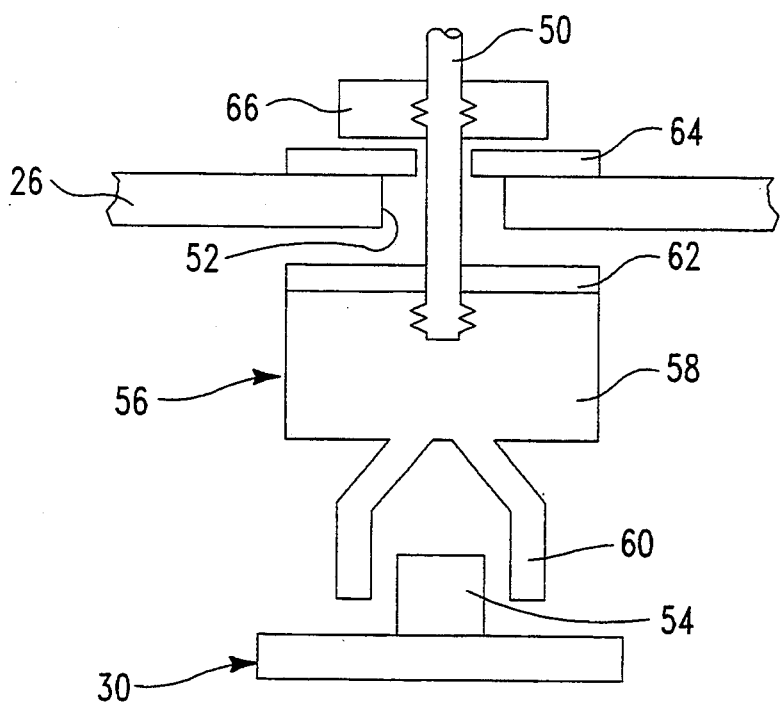
FIG. 5 is a further enlarge diagrammatic cross-sectional view from the right side and showing the lower portion of the sample support arrangement in greater detail.

It will be appreciated that air entering the oven chamber via the openings 28 in the ceiling 24 will sweep down over the analysis chamber ceiling 38, past the opening 37, where it creates a venturi effect, and back to exhaust openings 40 formed in the back wall 18 of the oven. The venturi effect operates to draw air out of the analysis chamber, which during the analysis is air laden with moisture evaporated during the analysis. Air may enter the analysis chamber at the upper front corners 42 of the side portions 36 (FIG. 3) beveled to also facilitate insertion of the muffling structure into the oven.

The analysis chamber centrally houses the sample support structure. Thus a four limbed support generally indicated by the numeral 44 includes equally spaced four upstanding posts of point supports 46 which terminate in a plane and support a fiber-glass pad placed thereon in a horizontal position. (The pad would bear the sample to be analyzed for its moisture content.) The posts 46 arise from limbs 48 mounted at their inner ends on the top of a stem 50. The stem 50 extends through an opening 52 in the floor 26 to rest on the load sensor 54 of the scale 30 below the floor.

The stem 50 rests on the load sensor 54 of scale 30 via a mount generally indicated by the numeral 56 to which it is suitably threaded. The mount 56 includes a head portion 58 having a threaded opening on its upper side for receiving the lower, threaded end of the stem 50 and being securely fastened thereto. The bottom of the head portion 58 is formed integral with a depending cylinder 60 open at its bottom end for being received on the scale load sensor 54. A weight 62 rests on the mount 56 to provide a low center of gravity and hence stability, as well as for zeroing-in of the electronic scale 30.

Loosely surrounding the stem 50 above the floor 26 is a microwave choke ring 64 to close off the floor opening 52 to loss of radiation.

Above the ring 64, the stem 50 is threaded to receive a threaded nut 66. During normal use of the oven, the nut 66 is spaced from the ring 64 to allow up and down movement of the stem 50 for weighing operations. However for shipping or other movement of the oven, the nut 66 is screwed down to react against the ring 64 and the floor 26 to hold the mount 56 off of the load sensor 54 and protect the sensitive electronic analytical balance or scale 30 against damage.

A somewhat dish-shaped microwave stirrer 67 is mounted in the oven behind the muffling structure 32 to insure adequate distribution of microwave radiation inserted into the oven from the conventional ceiling opening 68. The stirrer 67 has a drive shaft 70 extending downwards through the floor 26 opening 72 to a motor 74 therebeneath.

To modify a microwave oven 10 for use as an oven for moisture analyzing, the stirrer 66 would be installed in conventional fashion. Then the generally V-shaped structure 32 of the two-part muffling structure would be inserted so that the free ends of its side portions 36 were just inside the door 16 in closed position, the beveled corners 42 facilitating insertion. Then the ceiling 38 would be inserted to rest on the V-shaped structure 32 and complete the analysis chamber. Then the sample support structure 44 would be inserted through the floor opening 52 so that the lower end of the stem 50 could be screwed on to the mount 56. The mount 56 would then be raised so that it rested agains the bottom of the floor 26 and not on the load sensor 54 of the previously installed scale 30, by turning down the locking nut 66, to protect the scale during shipping.

In use, the user would first insure that the locking nut 60 had been unscrewed to allow the mount 56 to seat by gravity on the scale load sensor 54, and a fiber-glass pad 78 would be place on the support arrangement and the electronic analytical balance 30 zeroed-in. Then the sample 76 to be moisture analyzed would be placed on the fiber-glass pad 78 and the pad placed on the point supports 46. The oven door 16 would then be closed and the microwave oven turned-on. The electronic scale 30 and an electronic screen such as a vacuum flourescent display 82 would simultaneously be turned-on with the microwave oven so that the initial weight of the sample would be recorded and displayed, as well as subsequent weights periodically during during the desication being effected by the microwave oven radiation. The radiation period would have been previously determined from experimental testing showing when essentially all moisture has been evaporated from the sample. On termination of the microwave radiation, the printer would be activated, the printer recording being an indication of the per cent of the solids remaining after the moisture evaporation.

While applicant has shown and described a preferred embodiment of the invention, it will be apparent to those skilled in the art that other and different applications may be made of the principles of his invention. It is desired therefore to be limited only by the scope or spirit of the appended claims.

What is claimed is:

1. An apparatus for analyzing the moisture content of samples, comprising a microwave oven, and a structure formed of a microwave transparent material for isolating an analysis chamber therein, wherein the structure includes a back wall in the intermediate portion of the oven and wings projecting diagonally forward therefrom to the side walls of the oven, said structure providing a venturi effect when air is withdrawn from said analysis chamber.

2. An apparatus according to claim 1, wherein the oven includes a ceiling and the wings rise gradually in height from the back wall to the ceiling, and the structure also includes a roof for the chamber resting on the wings and sloping downward rearwardly.

3. An apparatus according to claim 2, wherein the back wall is not as high as the upper portions of the wings whose lower portions are projecting forward therefrom to define an empty space between the upper parts of those portions of the wings and between the back wall and the roof and constituting an opening between the analysis chamber and the rest of the oven.

4. An apparatus according to claim 1, further comprising a support arrangement in said analysis chamber for a pad bearing a sample to be analyzed for its moisture content.

5. An apparatus according to claim 4, wherein the support arrangement involves a set of at least three spaced posts on which the pad may rest.

6. An apparatus according to claim 5, further comprising a microwave stirrer in said oven outside of the analysis chamber.

7. An apparatus according to claim 4, wherein the oven has a raised floor and the support arrangement also includes a stem extending down through an opening in the raised floor of the oven.

8. An apparatus according to claim 7, wherein the apparatus includes a scale having a load sensor and mounted beneath the floor of the oven, and the lower end of the stem rests on the load sensor.

9. An apparatus according to claim 8, wherein a weight for zeroing the scale is mounted on said stem below said floor to provide maximum stability to the stem.

10. An apparatus according to claim 8, further comprising a microwave choke ring seal about said stem at said floor opening.

11. An apparatus according to claim 10, further comprising a locking nut on said stem for interacting with the floor to hold the stem out of effective engagement with the scale load sensor during shipment.

12. An apparatus according to claim 8, further comprising a locking nut on said stem for interacting with the floor to hold the stem out of effective engagement with the scale load sensor during shipment.

13. An apparatus according to claim 8, wherein the scale is an electronic one constantly measuring the weight of the sample and connected to a printer to record the measured weight and to an electronic screen to instantaneously display it.

14. In an apparatus for analyzing the moisture content of samples, comprising a microwave oven, and a structure formed of a microwave transparent material for isolating an analysis chamber therein, wherein the structure includes a back wall and wings projecting diagonally forward therefrom to the side walls of the oven, wherein the wings rise gradually in height from the back wall, and the structure also includes a roof for the chamber resting on the wings and sloping downward rearwardly, wherein the back wall is not as high as the portions of the wings projecting forward thereat to define an empty space between the upper parts of those portions of the wings and between the back wall and the roof and constituting an opening between the analysis chamber and the rest of the oven, further comprising means for supplying air above said chamber roof and exhausting it from the back of the oven so that air flows down over said roof and by said opening to provide a venturi effect withdrawing air from the analysis chamber.

15. An apparatus according to claim 14, wherein the apparatus includes a scale mounted below a raised floor of the oven and having a load sensor, further comprising a support arrangement in said analysis chamber for a pad bearing a sample to be analyzed for its moisture content, the support arrangement includes a set of at least three spaced posts on which the pad may rest and also includes a stem extending down through an opening in the raised floor of the oven and resting on the load sensor of a scale mounted beneath the raised floor of the oven.

* * * * *